(12) United States Patent
Zdeblick et al.

(10) Patent No.: US 7,974,705 B2
(45) Date of Patent: Jul. 5, 2011

(54) MULTIPLEXED MULTI-ELECTRODE NEUROSTIMULATION DEVICES

(75) Inventors: Mark Zdeblick, Portola Valley, CA (US); Todd Thompson, San Jose, CA (US); Marc Jensen, Los Gatos, CA (US); Olivier Colliou, Los Gatos, CA (US); Angela Strand, San Francisco, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 0 days.

(21) Appl. No.: 12/665,030

(22) PCT Filed: Nov. 13, 2009

(86) PCT No.: PCT/US2009/064468
§ 371 (c)(1),
(2), (4) Date: Dec. 16, 2009

(87) PCT Pub. No.: WO2010/057046
PCT Pub. Date: May 20, 2010

(65) Prior Publication Data
US 2011/0022124 A1   Jan. 27, 2011

Related U.S. Application Data

(60) Provisional application No. 61/114,433, filed on Nov. 13, 2008.

(51) Int. Cl.
*A61N 1/05* (2006.01)
(52) U.S. Cl. ............................ 607/117; 607/116; 607/38
(58) Field of Classification Search .............. 607/45–47, 607/115–120
See application file for complete search history.

(56) References Cited

U.S. PATENT DOCUMENTS

| | | |
|---|---|---|
| 5,114,424 A | 5/1992 | Hagen et al. |
| 5,328,442 A | 7/1994 | Levine |
| 5,370,672 A | 12/1994 | Fowler et al. |
| 5,400,784 A | 3/1995 | Durand et al. |
| 5,724,984 A | 3/1998 | Arnold et al. |
| 5,788,692 A | 8/1998 | Campbell et al. |
| 5,836,875 A | 11/1998 | Webster, Jr. |

(Continued)

FOREIGN PATENT DOCUMENTS

| | | |
|---|---|---|
| EP | 1048321 | 11/2000 |
| EP | 1426079 | 6/2004 |
| EP | 1938861 | 7/2008 |
| WO | WO 9952588 | 10/1999 |
| WO | WO 2004020040 | 3/2004 |
| WO | WO 2006073915 | 7/2006 |
| WO | WO 2008004010 | 1/2008 |
| WO | WO 2008008755 | 1/2008 |
| WO | WO 2008027639 | 3/2008 |

OTHER PUBLICATIONS

Kovacs, "Technology Development for a Chronic Neural Interface", A Dissertation, Stanford University Aug. 1990; pp. 9, 225-234, 257, 276.

*Primary Examiner* — Carl H Layno
*Assistant Examiner* — Paula J Stice
(74) *Attorney, Agent, or Firm* — Bret E. Field; Bozicevic Field & Francis LLP (57) ABSTRACT

Implantable stimulation devices are provided. Aspects of the devices include a multiplexed multi-electrode component configured for neural stimulation. The multiplexed multi-electrode component includes two or more individually addressable satellite electrode structures electrically coupled to a common conductor. The satellite structures include a hermetically sealed integrated circuit controller operatively coupled to one or more electrodes. Also provided are systems that include the devices of the invention, as well as methods of using the systems and devices in a variety of different applications.

9 Claims, 9 Drawing Sheets

U.S. PATENT DOCUMENTS

| | | | |
|---|---|---|---|
| 5,873,849 | A | 2/1999 | Bernard |
| 5,916,158 | A | 6/1999 | Webster, Jr. |
| 5,938,596 | A | 8/1999 | Woloszko et al. |
| 5,938,690 | A | 8/1999 | Law et al. |
| 6,006,124 | A | 12/1999 | Fischell et al. |
| 6,024,702 | A | 2/2000 | Iversen |
| 6,061,593 | A | 5/2000 | Fischell et al. |
| 6,064,905 | A | 5/2000 | Webster, Jr. et al. |
| 6,163,725 | A | 12/2000 | Peckham et al. |
| 6,167,311 | A | 12/2000 | Rezai |
| 6,241,724 | B1 | 6/2001 | Fleischman et al. |
| 6,259,937 | B1 | 7/2001 | Schulman et al. |
| 6,308,102 | B1 | 10/2001 | Sieracki et al. |
| 6,418,344 | B1 | 7/2002 | Rezai et al. |
| 6,459,745 | B1 | 10/2002 | Moose et al. |
| 6,473,653 | B1 | 10/2002 | Schallhorn et al. |
| 6,600,954 | B2 | 7/2003 | Cohen et al. |
| 6,609,030 | B1 | 8/2003 | Rezai et al. |
| 6,609,031 | B1 | 8/2003 | Law et al. |
| 6,654,642 | B2 | 11/2003 | North et al. |
| 6,708,064 | B2 | 3/2004 | Rezai |
| 6,745,079 | B2 | 6/2004 | King |
| 6,748,276 | B1 | 6/2004 | Daignault, Jr. et al. |
| 6,856,822 | B2 | 2/2005 | Larsson |
| 6,871,099 | B1 | 3/2005 | Whitehurst et al. |
| 6,895,280 | B2 | 5/2005 | Meadows et al. |
| 6,895,283 | B2 | 5/2005 | Erickson et al. |
| 6,993,384 | B2 | 1/2006 | Bradley et al. |
| 7,010,356 | B2 | 3/2006 | Jog et al. |
| 7,047,082 | B1 | 5/2006 | Schrom et al. |
| 7,047,084 | B2 | 5/2006 | Erickson et al. |
| 7,142,923 | B2 | 11/2006 | North et al. |
| 7,146,219 | B2 | 12/2006 | Sieracki et al. |
| 7,146,224 | B2 | 12/2006 | King |
| 7,174,218 | B1 | 2/2007 | Kuzma |
| 7,181,286 | B2 | 2/2007 | Sieracki et al. |
| 7,181,288 | B1 | 2/2007 | Rezai et al. |
| 7,214,189 | B2 | 5/2007 | Zdeblick |
| 7,216,000 | B2 | 5/2007 | Sieracki et al. |
| 7,231,254 | B2 | 6/2007 | DiLorenzo |
| 7,239,918 | B2 | 7/2007 | Strother et al. |
| 7,254,445 | B2 | 8/2007 | Law et al. |
| 7,292,890 | B2 | 11/2007 | Whitehurst et al. |
| 7,324,852 | B2 | 1/2008 | Barolat et al. |
| 7,330,764 | B2 | 2/2008 | Swoyer et al. |
| 7,333,857 | B2 | 2/2008 | Campbell |
| 7,337,006 | B2 | 2/2008 | Kim et al. |
| 7,346,398 | B2 | 3/2008 | Gross et al. |
| 7,349,743 | B2 | 3/2008 | Tadlock |
| 7,369,897 | B2 | 5/2008 | Boveja et al. |
| 7,373,206 | B2 | 5/2008 | Sieracki et al. |
| 7,386,348 | B2 | 6/2008 | North et al. |
| 7,395,118 | B2 | 7/2008 | Erickson |
| 7,403,820 | B2 | 7/2008 | DiLorenzo |
| 7,415,309 | B2 | 8/2008 | McIntyre |
| 7,447,546 | B2 | 11/2008 | Kim et al. |
| 7,450,993 | B2 | 11/2008 | Kim et al. |
| 7,467,016 | B2 | 12/2008 | Colborn |
| 7,502,651 | B2 | 3/2009 | Kim et al. |
| 7,580,753 | B2 | 8/2009 | Kim et al. |
| 2001/0000187 | A1 | 4/2001 | Peckham et al. |
| 2001/0025192 | A1 | 9/2001 | Gerber et al. |
| 2002/0099419 | A1 | 7/2002 | Cohen et al. |
| 2002/0193859 | A1 | 12/2002 | Schulman et al. |
| 2003/0093130 | A1 | 5/2003 | Stypulkowski |
| 2004/0015205 | A1 | 1/2004 | Whitehurst et al. |
| 2004/0024440 | A1 | 2/2004 | Cole |
| 2004/0039417 | A1 | 2/2004 | Soykan et al. |
| 2004/0059392 | A1 | 3/2004 | Parramon et al. |
| 2004/0059395 | A1 | 3/2004 | North et al. |
| 2004/0093053 | A1 | 5/2004 | Gerber et al. |
| 2004/0098074 | A1 | 5/2004 | Erickson et al. |
| 2004/0193021 | A1 | 9/2004 | Zdeblick |
| 2004/0199235 | A1 | 10/2004 | Younis |
| 2005/0010262 | A1 | 1/2005 | Rezai et al. |
| 2005/0070982 | A1 | 3/2005 | Heurth et al. |
| 2005/0075681 | A1 | 4/2005 | Rezai et al. |
| 2005/0131506 | A1 | 6/2005 | Rezai et al. |
| 2005/0177192 | A1 | 8/2005 | Rezai et al. |
| 2005/0246004 | A1 | 11/2005 | Cameron et al. |
| 2005/0267542 | A1 | 12/2005 | David et al. |
| 2005/0283200 | A1 | 12/2005 | Rezai et al. |
| 2005/0283201 | A1 | 12/2005 | Machado et al. |
| 2005/0288760 | A1 | 12/2005 | Machado et al. |
| 2006/0004424 | A1 | 1/2006 | Loeb et al. |
| 2006/0020297 | A1 | 1/2006 | Gerber et al. |
| 2006/0058588 | A1* | 3/2006 | Zdeblick ............... 600/300 |
| 2006/0122654 | A1 | 6/2006 | Bradley et al. |
| 2006/0122678 | A1 | 6/2006 | Olsen et al. |
| 2006/0142802 | A1 | 6/2006 | Armstrong |
| 2006/0167525 | A1 | 7/2006 | King |
| 2006/0168805 | A1 | 8/2006 | Hegland et al. |
| 2006/0173262 | A1 | 8/2006 | Hegland et al. |
| 2006/0195145 | A1 | 8/2006 | Lee et al. |
| 2006/0212093 | A1 | 9/2006 | Pless et al. |
| 2006/0224222 | A1 | 10/2006 | Bradley et al. |
| 2006/0247539 | A1 | 11/2006 | Schugt et al. |
| 2006/0253182 | A1 | 11/2006 | King |
| 2006/0258950 | A1 | 11/2006 | Hargrove et al. |
| 2006/0265038 | A1 | 11/2006 | Hagen et al. |
| 2007/0010858 | A1 | 1/2007 | Forsberg |
| 2007/0060970 | A1 | 3/2007 | Burdon et al. |
| 2007/0060980 | A1 | 3/2007 | Strother et al. |
| 2007/0060991 | A1 | 3/2007 | North et al. |
| 2007/0066995 | A1 | 3/2007 | Strother et al. |
| 2007/0067000 | A1 | 3/2007 | Strother et al. |
| 2007/0100399 | A1 | 5/2007 | Parramon et al. |
| 2007/0123944 | A1 | 5/2007 | Zdeblick |
| 2007/0123956 | A1 | 5/2007 | Sieracki et al. |
| 2007/0162086 | A1 | 7/2007 | DiLorenzo |
| 2007/0167991 | A1 | 7/2007 | DiLorenzo |
| 2007/0168008 | A1 | 7/2007 | Olsen |
| 2007/0173896 | A1 | 7/2007 | Zdeblick |
| 2007/0173897 | A1 | 7/2007 | Zdeblick |
| 2007/0179569 | A1 | 8/2007 | Zdeblick |
| 2007/0179579 | A1 | 8/2007 | Feler et al. |
| 2007/0185537 | A1 | 8/2007 | Zdeblick |
| 2007/0185548 | A1 | 8/2007 | Zdeblick |
| 2007/0185549 | A1 | 8/2007 | Zdeblick |
| 2007/0198066 | A1 | 8/2007 | Greenberg et al. |
| 2007/0219608 | A1 | 9/2007 | Swoyer et al. |
| 2007/0255336 | A1 | 11/2007 | Herbert et al. |
| 2007/0255373 | A1 | 11/2007 | Metzler et al. |
| 2007/0265678 | A1 | 11/2007 | Sieracki et al. |
| 2007/0282389 | A1 | 12/2007 | Moxon et al. |
| 2007/0293906 | A1 | 12/2007 | Cowan et al. |
| 2007/0293909 | A1 | 12/2007 | Cowan et al. |
| 2007/0293910 | A1 | 12/2007 | Strother et al. |
| 2007/0299483 | A1 | 12/2007 | Strother et al. |
| 2008/0021292 | A1 | 1/2008 | Stypulkowski |
| 2008/0021503 | A1 | 1/2008 | Whitehurst et al. |
| 2008/0027289 | A1 | 1/2008 | Zdeblick |
| 2008/0039916 | A1 | 2/2008 | Colliou et al. |
| 2008/0045826 | A1 | 2/2008 | Greenberg et al. |
| 2008/0046059 | A1 | 2/2008 | Zarembo et al. |
| 2008/0058872 | A1 | 3/2008 | Brockway et al. |
| 2008/0058899 | A1 | 3/2008 | Sieracki et al. |
| 2008/0061630 | A1 | 3/2008 | Andreu et al. |
| 2008/0065182 | A1 | 3/2008 | Strother et al. |
| 2008/0077186 | A1 | 3/2008 | Thompson et al. |
| 2008/0091246 | A1 | 4/2008 | Carey et al. |
| 2008/0097529 | A1 | 4/2008 | Parramon et al. |
| 2008/0097566 | A1 | 4/2008 | Colliou |
| 2008/0114230 | A1 | 5/2008 | Addis |
| 2008/0125833 | A1 | 5/2008 | Bradley et al. |
| 2008/0132974 | A1 | 6/2008 | Strother et al. |
| 2008/0139913 | A1 | 6/2008 | Schulman |
| 2008/0140141 | A1 | 6/2008 | Ben-David et al. |
| 2008/0140152 | A1 | 6/2008 | Imran et al. |
| 2008/0140153 | A1 | 6/2008 | Burdulis |
| 2008/0140167 | A1 | 6/2008 | Hagen et al. |
| 2008/0140169 | A1 | 6/2008 | Imran |
| 2008/0140170 | A1 | 6/2008 | Filloux et al. |
| 2008/0147145 | A1 | 6/2008 | Sieracki et al. |
| 2008/0147156 | A1 | 6/2008 | Imran |
| 2008/0154328 | A1 | 6/2008 | Thompson et al. |
| 2008/0154332 | A1 | 6/2008 | Rezai |

| | | | | | | |
|---|---|---|---|---|---|---|
| 2008/0167698 A1 | 7/2008 | Kim et al. | | 2008/0208305 A1 | 8/2008 | Rezai et al. |
| 2008/0177343 A1 | 7/2008 | Dal Molin et al. | | 2008/0215101 A1 | 9/2008 | Rezai et al. |
| 2008/0183221 A1 | 7/2008 | Burdulis | | 2008/0234791 A1 | 9/2008 | Arle et al. |
| 2008/0183224 A1 | 7/2008 | Barolat | | 2008/0243214 A1 | 10/2008 | Koblish |
| 2008/0183248 A1 | 7/2008 | Rezai et al. | | 2008/0255647 A1 | 10/2008 | Jensen et al. |
| 2008/0183257 A1 | 7/2008 | Imran et al. | | 2008/0294062 A1 | 11/2008 | Rapoport et al. |
| 2008/0183258 A1 | 7/2008 | Inman | | 2009/0024184 A1 | 1/2009 | Sun et al. |
| 2008/0188909 A1 | 8/2008 | Bradley | | | | |
| 2008/0208284 A1 | 8/2008 | Rezai et al. | | * cited by examiner | | |

MULTIPLEXED MULTI-ELECTRODE NEUROSTIMULATION DEVICES

RELATED APPLICATION AND CROSS REFERENCE

This application claims the benefit of U.S. Provisional Application Ser. No. 61/114,433 filed on Nov. 13, 2008, the entire disclosure of which is incorporated herein by reference.

FIELD OF THE INVENTION

The present invention is related to electrical devices and systems for stimulation of a target site and, more specifically, multiplexed rechargeable leads including multiple electrodes that are individually addressable and include an inductive power source and power storage units.

BACKGROUND

Implantable neurostimulators are used to deliver neurostimulation therapy to patients to treat a variety of symptoms or conditions such as chronic pain, tremor, Parkinson's disease, epilepsy, incontinence, or gastroparesis. Implantable neurostimulators may deliver neurostimulation therapy in the form of electrical pulses via implantable leads that include electrodes. To treat the above-identified symptoms or conditions, implantable leads may be implanted along nerves, within the epidural or intrathecal space of the spinal column, and around the brain, or other organs or tissue of a patient, depending on the particular condition that is sought to be treated with the device.

With respect to implantable leads, several elements such as conductors, electrodes and insulators may be combined to produce a lead body. A lead may include one or more conductors extending the length of the lead body from a distal end to a proximal end of the lead. The conductors electrically connect one or more electrodes at the distal end to one or more connectors at the proximal end of the lead. The electrodes are designed to form an electrical connection or stimulus point with tissue or organs. Lead connectors (sometimes referred to as terminals, contacts, or contact electrodes) are adapted to electrically and mechanically connect leads to implantable pulse generators or RF receivers (stimulation sources), or other medical devices. An insulating material may form the lead body and surround the conductors for electrical isolation between the conductors and for protection from the external contact and compatibility with a body.

Such leads may be implanted into a body at an insertion site and extend from the implant site to the stimulation site (area of placement of the electrodes). The implant site may be a subcutaneous pocket that receives and houses the pulse generator or receiver (providing a stimulation source). The implant site may be positioned a distance away from the stimulation site, such as near the buttocks or other place in the torso area. One common configuration is to have the implant site and insertion site located in the lower back area, with the leads extending through the epidural space in the spine to the stimulation site, such as middle back, upper back, neck or brain areas.

Current lead designs have different shapes, such as those commonly known as paddle leads and percutaneous leads. Paddle leads, which are typically larger than percutaneous leads, are directional and often utilized due to desired stimulus effect on the tissues or areas. However, current paddle leads require insertion using surgical means, and hence, removal through surgical means. Percutaneous leads are designed for easy introduction into the epidural space using a special needle. Therefore, such leads are typically smaller and more nearly circular in cross-section than paddle-shaped leads. This reduced size facilitates their implantation in the body, allows their implantation into more areas of the body, and minimizes the unwanted side effects of their implantation.

SUMMARY

Implantable neural stimulation devices are provided. Aspects of the devices include a multiplexed multi-electrode component configured for neural stimulation. The multiplexed multi-electrode component includes two or more individually addressable satellite electrode structures electrically coupled to a common conductor. The satellite structures include a hermetically sealed integrated circuit controller operatively coupled to one or more electrodes. Also provided are systems that include the devices of the invention, as well as methods of using the systems and devices in a variety of different applications.

DETAILED DESCRIPTION

Implantable neural stimulation devices are provided. Aspects of the devices include a multiplexed multi-electrode component configured for neural stimulation. The multiplexed multi-electrode component includes two or more individually addressable satellite electrode structures electrically coupled to a common conductor. The individually addressable satellite electrode structures include a hermetically sealed integrated circuit controller operatively coupled to one or more electrodes. Also provided are systems that include the devices of the invention, as well as methods of using the systems and devices in a variety of different applications.

In further describing various aspects of the invention, devices of the invention are reviewed first in greater detail, followed by a description of systems and methods of using the same in various applications, including neural stimulation applications.

Figures 1, 1A:
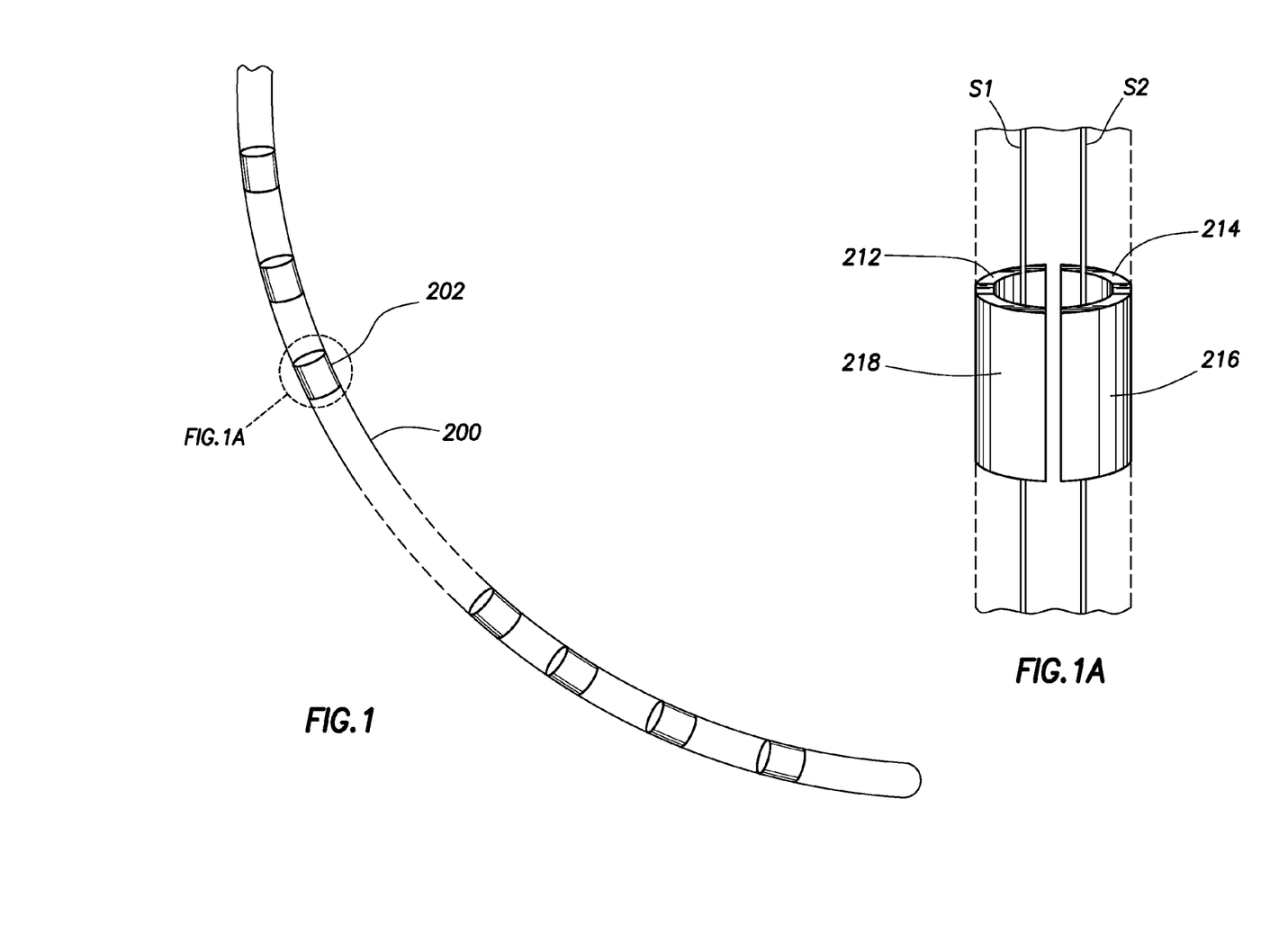
FIG. 1 provides a view of percutaneous lead according to an aspect of the invention, where the percutaneous lead includes several individually addressable satellite electrode structures.
FIG. 1A provides an exploded view of an electrode structure of the lead of FIG. 1
Figure 1B:
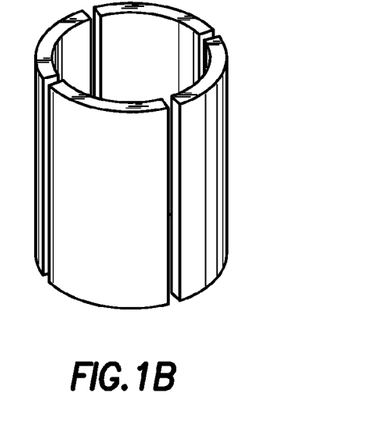
FIG. 1B & FIG. 1C provide exploded views of the electrode structure of FIG. 1 with four and six electrodes, respectively.
Figure 1C:
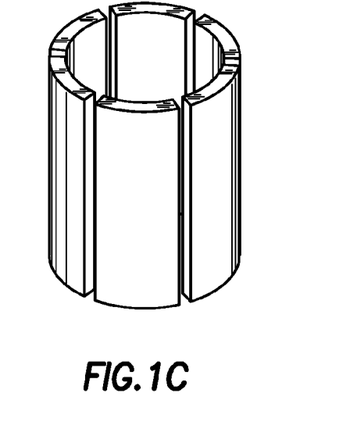

FIG. 1 shows a lead 200 including multiplexed multi-electrode components that are individually addressable satellite structures 202 positioned longitudinally on the lead 200. The lead 200 includes two bus wires S1 and S2, which are coupled to individually addressable electrode satellite structures, such as individually addressable satellite electrode structure 202. FIG. 1A also shows individually addressable satellite electrode structure 202 with an enlarged view. Individually addressable satellite electrode structure 202 includes electrodes 212, 214, 216, and 218, located in the four quadrants of the cylindrical outer walls of satellite 202. FIG. 1B provides a depiction of the arrangement of four electrodes. As indicated above, a given individually addressable satellite electrode structure may include more or less than four electrode elements. For example, six electrode elements may be present, as shown in FIG. 1C. Each individually addressable satellite electrode structure also contains integrated circuit component inside the structure which communicates with other satellite structures and/or distinct control units, e.g., to receive neurostimulation signals and/or configuration signals that determine which of the different electrodes are to be coupled to bus wires S1 or S2 of FIG. 1A.

Figure 2:
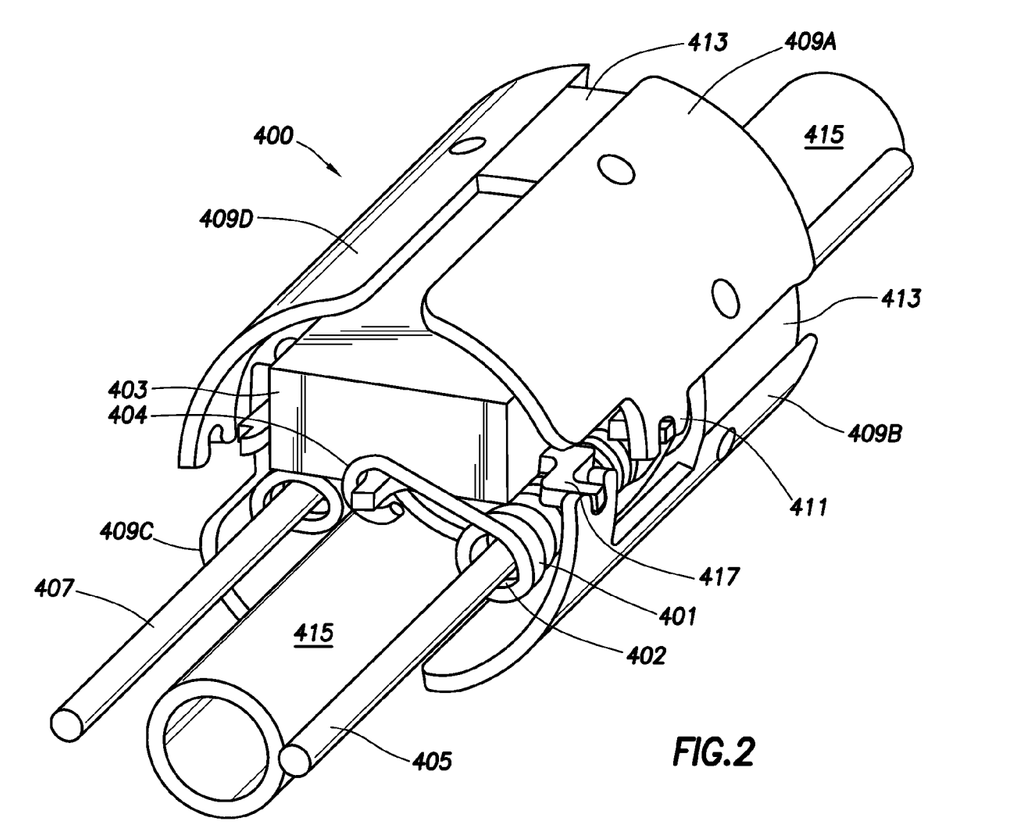
FIG. 2 provides a more detailed view of an individually addressable satellite electrode structure as may be present in a lead according to the invention.

FIG. 2 shows a more detailed view of one type of individually addressable segmented electrode structure 400. The configuration shown in FIGS. 1A, 1B and 2 may be viewed as a quadrant electrode. As shown in FIG. 2, flexible connections 401 are provided between a hermetically sealed element 403 and elongated conductive members 405 and 407, similar to the conductive members S1 and S2 of FIG. 1. This design creates a flexible connection between the element 403 and the elongated conductive members 405 and 407. Additionally, the connections 401 each include a securing element 404 to hold the element 403 in place. According to one aspect of the invention, the element 403 is an integrated circuit and according to another aspect of the invention the element 403 is a housing that contains multiple components, including a power storage unit and an integrated circuit. As shown, the elongated conductive members 405 and 407 are placed into an inner lumen 402 of the flexible connections 401. The element 403 will be referenced hereinafter as integrated circuit 403 according to one aspect of the invention and for illustrative purposes. The integrated circuit 403 is attached to four distinct electrodes 409A, 409B, 409C and 409D by junctures 411 and 417, which are also present on the opposite side of the structure 400, but not shown. The electrodes 409A, 409B, 409C and 409D are joined together in a suitable configuration structure 413, which may be made of any convenient material, such as polyetheretherketone (PEEK). A guide wire lumen 415 runs beneath integrated circuit 403 and beneath and/or between elongated conductive members 405 and 407, all running through or contained with the area defined by the electrodes 409A, 409B, 409C and 409D.

Additional details regarding individually addressable satellite electrode structures can be found in PCT application serial no. PCT/US2005/031559 published as WO 2006/029090; PCT application serial no. PCT/US2005/046815 published as WO 2006/069323; PCT application serial no. PCT/US2005/046811 published as WO 2006/069322; and U.S. application Ser. No. 11/939,524 published as US 2008-0114230 A1; the disclosures of which are herein incorporated by reference.

As summarized above, implantable neural stimulation devices are provided. The implantable neural stimulation devices are configured for neural stimulation. As such, they are structured specifically for neural stimulation applications, in terms of device form factor or shape, as well as control unit programming. Devices of the invention may have a variety of shapes that are suitable for use in neural stimulation applications, including shapes found in traditional percutaneous leads, paddle leads as well as other neurostimulation specific configurations. Programming (a set of instructions that are implemented by a processor to perform a given task) that is specific for neural stimulation protocols may also be included in components of devices of the invention, such as integrated circuit elements of the individually addressable satellite electrode structures of the devices. Programming that may be part of the devices may include a full set of instructions for a given task or a partial set of instructions that is employed in conjunction with other instructions associated with components distinct from the devices, where such additional instructions may be present in a distinct implantable control unit to which the device may be operatively coupled during use.

As the devices of the invention are implantable, they are configured to maintain functionality when present in a physiological environment, including a high salt, high humidity environment found inside of a body. Implantable devices of the invention are configured to maintain functionality under these conditions for two or more days, such as one week or longer, four weeks or longer, six months or longer, one year or longer, including five years or longer. In some instances, the implantable devices are configured to maintain functionality when implanted at a physiological site for a period ranging from one to eighty years or longer, such as from five to seventy years or longer, and including for a period ranging from ten to fifty years or longer.

Devices of invention include a multiplexed multi-electrode component. Multiplexed multi-electrode components include two or more electrodes which are electrically coupled, either directly or through an intermediate connector, to a common conductor or set of common conductors, such that the two or more electrodes share one or more conductors. The term "conductor" refers to a variety of configurations of electrically conductive elements, including wires, cables, etc. A variety of different structures may be implemented to provide the multiplex configuration. Multiplex configurations of interest include, but are not limited to, those described in: PCT application no. PCT/US2003/039524 published as WO 2004/052182; PCT application no. PCT/US2005/031559 published as WO 2006/029090; PCT application no. PCT/US2005/046811 published as WO 2006/069322; PCT application no. PCT/US2005/046815 published as WO 2006/069323; and PCT application no. PCT US2006/048944 published as WO 2007/075974; the disclosures of which are herein incorporated by reference.

The multiplexed multi-electrode components include two or more individually addressable satellite electrode structures. In some instances, more than two individually addressable satellite structures are present in the device, such as three or more, four or more, five or more, six or more, ten or more, twenty or more (including twenty-four), thirty or more, fifty or more, etc. Individually addressable satellite electrode structures are those that can be individually controlled from a site remote from the satellite electrode structure, such as a separate implanted control unit to which the device is operatively coupled or to an extracorporeal control unit.

Satellite electrode structures are structures that include an integrated circuit control device and at least one electrode element. The satellite electrode structures of the invention include control circuitry in the form of an integrated circuit that imparts addressability to the satellite electrode structure. Integrated circuit components of the structures are constructs that include circuitry components and a solid support. The solid support may be small, for example where it is dimensioned to have a width ranging from 0.01 mm to 100 mm, such as from 0.1 mm to 20 mm, and including from 0.5 mm to 2 mm; a length ranging from 0.01 mm to 100 mm, such as from 0.1 mm to 20 mm, and including from 0.5 mm to 2 mm, and a height ranging from 0.01 mm to 10 mm, including from 0.05 mm to 2 mm, and including from 0.1 mm to 0.5 mm. The solid support element may take a variety of different configurations, such as but not limited to: a chip configuration, a cylinder configuration, a spherical configuration, a disc configuration, etc. A particular configuration may be selected based on intended application, method of manufacture, etc. While the material from which the solid support is fabricated may vary considerably depending on the particular device for which the device is configured for use, in certain instances the solid support is made up of a semiconductor material, such as silicon.

Integrated circuit components of the individually addressable satellite electrode structures may include a number of distinct functional blocks, i.e., modules. In some instances, the circuits include at least the following functional blocks: a power extraction functional block; an energy storage functional block; a sensor functional block; a communication functional block; and a device configuration functional block, etc.

Within a given satellite electrode structure, at least some of, e.g., two or more, up to and including all of, the functional blocks may be present in a single integrated circuit. By single integrated circuit is meant a single circuit structure that includes all of the different desired functional blocks for the device. In these types of structures, the integrated circuit is a monolithic integrated circuit that is a miniaturized electronic circuit which may be made up of semiconductor and passive components that have been manufactured in the surface of a thin substrate of semiconductor material. Sensors of the invention may also include integrated circuits that are hybrid integrated circuits, which are miniaturized electronic circuits constructed of individual semiconductor devices, as well as passive components, bonded to a substrate or circuit board.

A given satellite electrode structure may include a single electrode element coupled to an integrated circuit, or two or more electrodes coupled to the same integrated circuit, such as three or more electrodes, four or more electrodes, six or more electrodes, etc. In various aspects, the structure includes two or more electrode elements, such as three or more electrode elements, including four or more electrode elements, e.g., where the structure is a segmented electrode structure. The various electrode elements may be positioned in three-dimensional space relative to their controlling integrated circuit to which they are electronically coupled in a number of different ways. For example, the multiple electrode elements may be radially distributed, i.e., axially uniformly positioned, about an integrated circuit. Alternatively, the multiple electrode elements may be positioned to one side of an integrated circuit.

Individually addressable satellite electrode structures of the devices have hermetically sealed integrated circuit components, such that they include a sealing element which seals the integrated circuit from the implanted environment so that the structure maintains functionality, at least for the intended lifespan of the device. The nature of the sealing element may vary, so long as it maintains the functionality of the satellite structure in the implanted environment for the desired period of time, such as one week or longer, one month or longer, one year or longer, five years or longer, ten years or longer, twenty-five years or longer, forty years or longer.

In some instances, the sealing element is a conformal, void-free sealing layer, where the sealing layer is present on at least a portion of the outer surface of the integrated circuit component (described above). In some instances, this conformal, void-free sealing layer may be present on substantially all of the outer surfaces of the integrated circuit component. Alternatively, this conformal, void-free sealing layer may be present on only some of the surfaces of the integrated circuit, such as on only one surface or even just a portion of one surface of the integrated circuit component. As such, some sensors have an integrated circuit component completely encased in a conformal, void free sealing layer. Other sensors are configured such that only the top surface of an integrated circuit component is covered with the conformal, void-free sealing layer.

The conformal, void-free sealing layer may be a "thin-film" coating, in that its thickness is such that it does not substantially increase the total volume of the integrated circuit structure with which it is associated, where any increase in volume of the structure that can be attributed to the layer may be 10% or less, such as 5% or less, including 1% or less by volume. In some instances, the seal layer has a thickness in a range from 0.1 to 10.0 µm, such as in a range from 0.3 to 3.0 µm thick, and including in a range 1.0 µm thick.

The seal layer may be produced on the integrated circuit component using any of a number of different protocols, including but not limited to planar processing protocols, such as plasma-enhanced-chemical-vapor deposition, physical-vapor deposition, sputtering, evaporation, cathodic-arc deposition, low-pressure chemical-vapor deposition, etc.

Additional description of conformal, void-free sealing layers that may be employed for sensors of the invention is provided in PCT application serial no. PCT/US2007/009270 published under publication no. WO/2007/120884, the disclosure of which is herein incorporated by reference.

Also of interest as sealing elements are corrosion-resistant holders having at least one conductive feed-through and a sealing layer; where the sealing layer and holder are configured to define a hermetically sealed container that encloses the integrated circuit component. The conductive feed-through may be a metal, such as platinum, iridium etc., an alloy of metal and a semiconductor, a nitride, a semiconductor or some other convenient material. In some instances, the corrosion-resistant holder comprises silicon or a ceramic. While dimensions may vary, the corrosion-resistant holder may have walls that are at least 1 µm thick, such as at least 50 µm thick, where the walls may range from 1 to 125 µm, including from 25 to 100 µm. The sealing layer may be metallic, where metals of interest include noble metals and alloys thereof, such as platinum and platinum alloys. Dimensions of the sealing layer may also vary, ranging in some instances from 0.5 µm thick or thicker, such as 2.0 µm thick or thicker, and including 20 µm thick or thickness, where sealing layer thicknesses may range from 0.5 to 100 µm, such as from 1 to 50 µm. In certain configurations, the structure further includes an insulative material present in the hermetically sealed volume. In some cases, the hermetically sealed volume ranges from 1 pl. to 1 ml.

In some instances, the in-vivo corrosion-resistant holder is a structure configured to hold an integrated circuit component such that the integrated circuit component is bounded on all but one side by the walls of the holder. For example, the holder may include side walls and a bottom, where the holder may have a variety of different configurations as long as it contains the integrated circuit component in a manner such that the component is held in a volume bounded on all but one side. Accordingly, the shape of the holder may be square, circular, ovoid, rectangular, or some other shape as desired.

Additional description of corrosion resistant holders that may be employed for sensors of the invention is provided in PCT application serial no. PCT/US2005/046815 published under publication no. WO/2006/069323, the disclosure of which is herein incorporated by reference.

As indicated above, multiplexed multi-electrode components of the invention may include a single multiplexed lead element along which the two or more, such as ten or more, twenty or more, or even twenty four or more individually addressable satellite electrode structures are longitudinally or otherwise positioned along the multiplexed lead. By single multiplexed lead element is meant that the multiplex component and two or more individually addressable satellite structures are integrated into the same physical lead structure, such that the multiplexed multi-electrode component is not made up of two or more distinct, readily separable components that are coupled together.

Figure 3A:
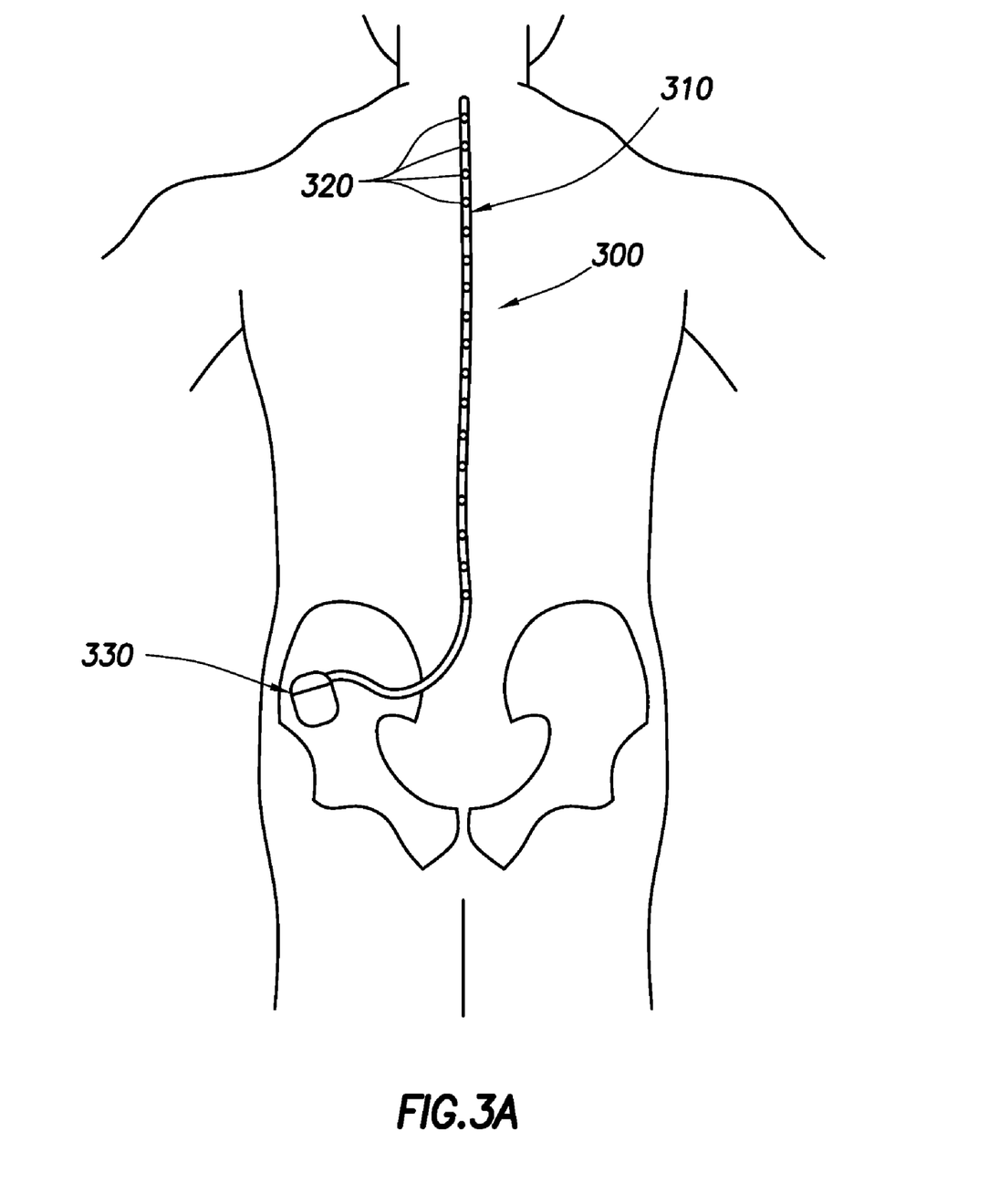
FIGS. 3A to 3E provide views of a percutaneous neurostimulation system and components thereof according to one aspect of the invention.

Another example of a multiplexed multi-electrode component that is made up of a single multiplexed lead element is shown in FIG. 3A. In FIG. 3A, device 300 includes a multiplexed lead 310 which is configured for neural stimulation by being structured to be placed along the spine in the epidural space. The lead 310 extends along a substantial length of the spine, for example, fifty percent or more, such as seventy-five percent or more, including eighty percent or more of the length of the spine. Distributed longitudinally along the length of the lead 310 are individually addressable satellite electrode structures 320. The lead 310 is operatively coupled to a control unit 330 via a suitable connection, such as an IS-1 connection.

Figure 3B:
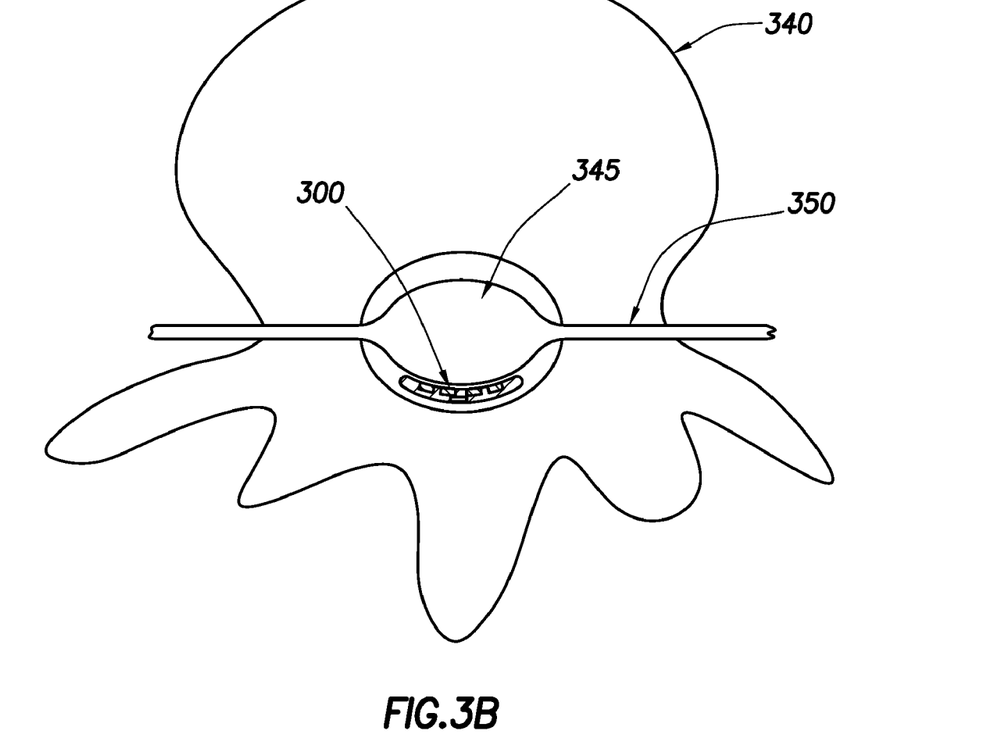
Figure 3C:
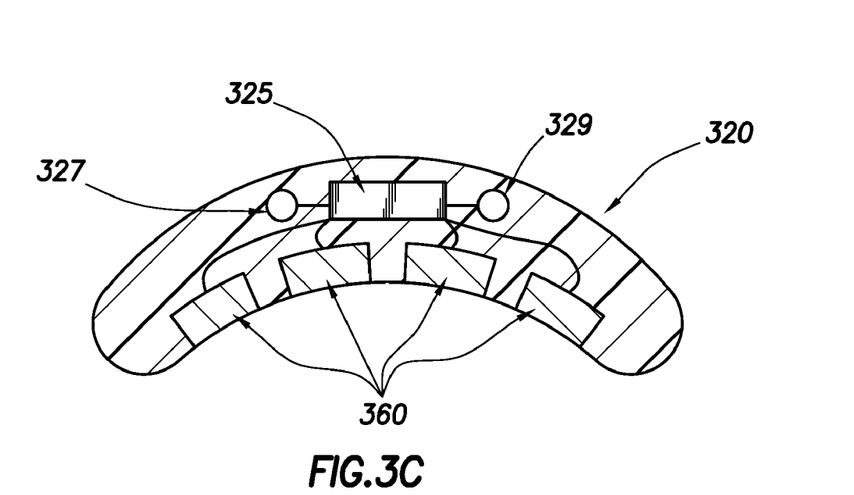

FIG. 3B, a cross-section of vertebral body 340 is shown with spinal cord 345 and spinal nerve 350. Also shown is a portion of the device 300 in cross section. The device 300 is configured for neural stimulation as the cross-section of device 300 is shaped to conform to the surface of spinal cord 345. FIG. 3C provides a more detailed view of the cross-section of device 300. As shown in FIG. 3C, an individually addressable satellite structure 320 is shown having hermetically sealed integrated circuit component 325 coupled to common conductors 327 and 329 as well as four electrodes 360.

Referring now to FIG. 3C, the electrodes 360 are positioned to one side of integrated circuit 325 of the device 300. Where desired, the electrodes 360 are part of a given individually addressable satellite electrode structure 320 and may have a staggered configured, such as the configuration shown in FIG. 3D.

Figure 3D:
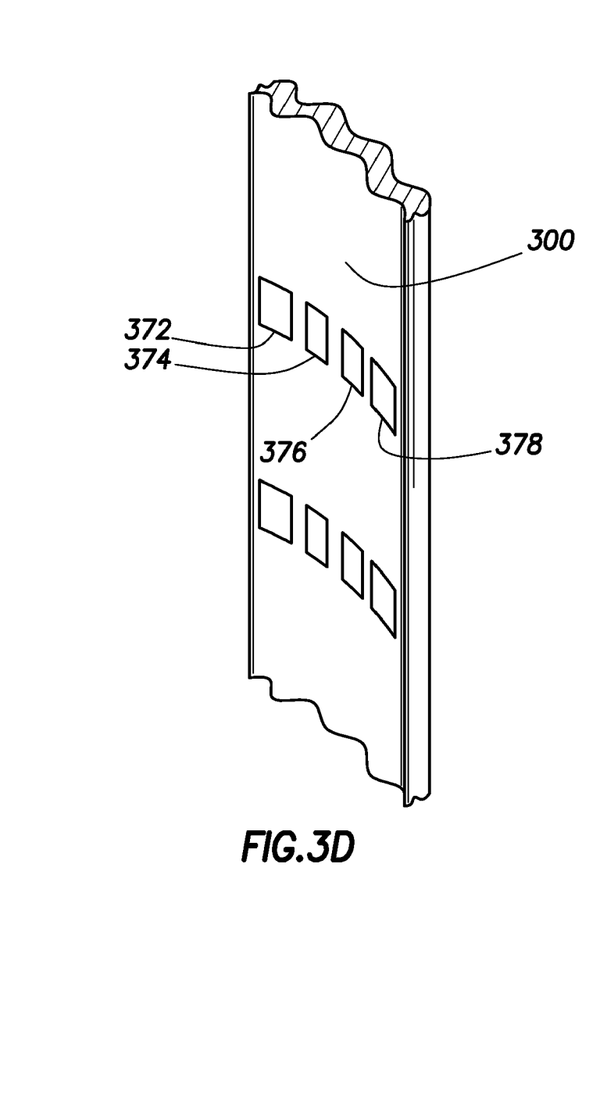

Referring now to FIG. 3D, electrodes 372, 374, 376 and 378 are positioned along one side of device 300 in a staggered configuration.

Figure 3E:
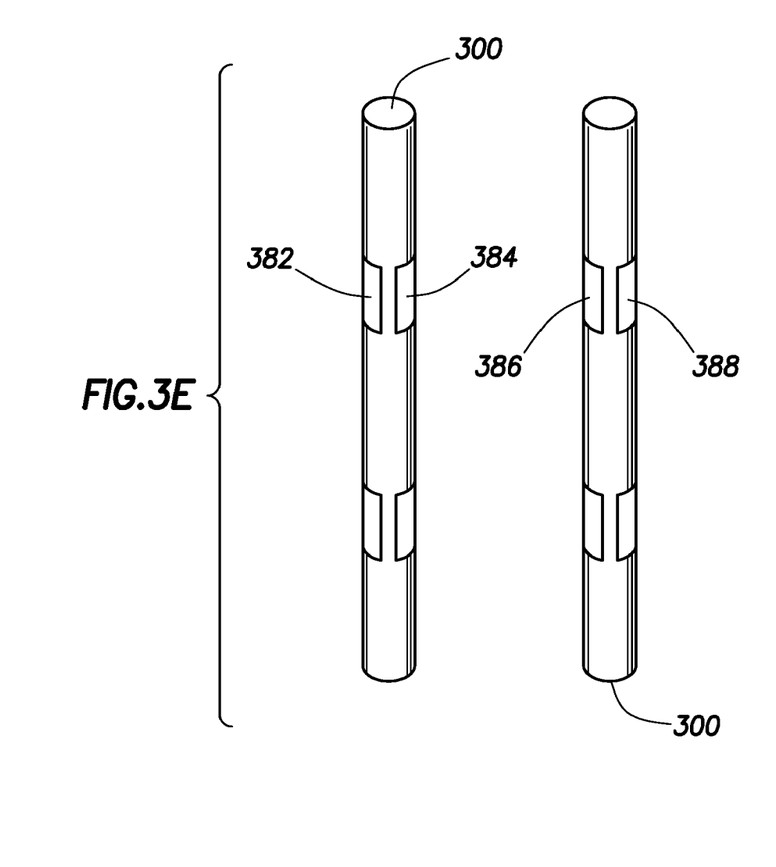

Referring now to FIG. 3E, both sides of the device 300 are shown for clarity. This configuration includes four electrodes 382, 384, 386, and 388 positioned radially on device 300, and in fact uniformly axially positioned about the lead element of the device 300.

In alternative configurations to those described above, multiplexed multi-electrode lead components of the devices may also be made up of two or more distinct sub-components that are operatively coupled to each other to produce the multiplexed multi-electrode lead component. For example, multiplexed multi-electrode lead components of the invention may include a first subcomponent that is made up of a multiplexed lead (such as a lead having three or fewer, such as two or fewer conductive elements) and a second subcomponent that includes two or more individually addressable satellite electrode structures.

Figure 4:
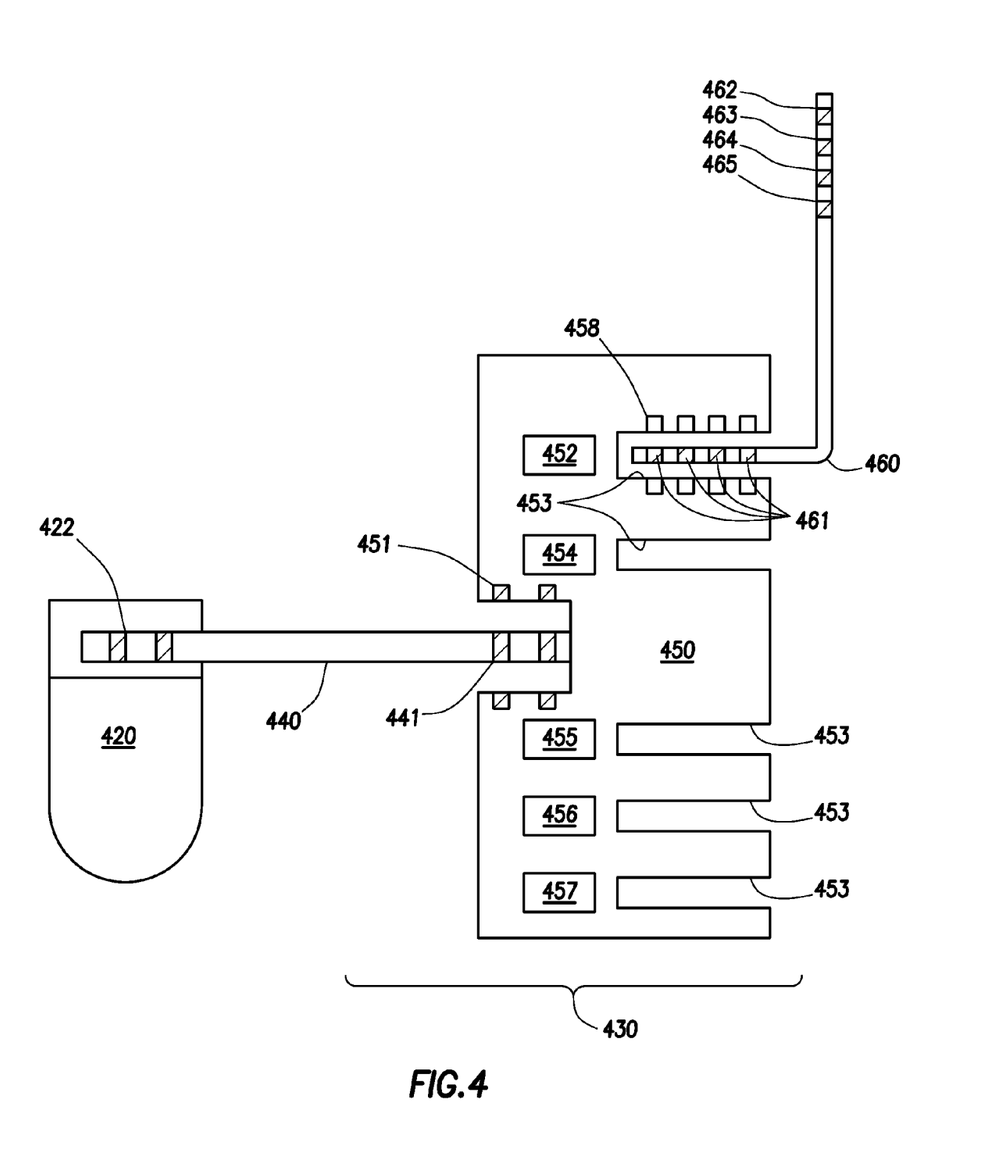
FIG. 4 provides a view of a multi-port connector that may be present in a system according to the invention.

Referring now to FIG. 4, an implantable controller 420 is shown connected to a multiplexed multi-electrode component 430 through a multiplexed lead 440. The controller 420 is connected to the multiplexed lead 440 via an IS-1 connection 422. The multiplexed lead 440 is electrically coupled to a multi-port connector 450, wherein the multi-port connector 450 includes five distinct individually addressable satellite integrated circuits 452, 454, 455, 456, and 457, where an individually addressable satellite structure is provided for each electrode lead port 453. Also shown is an electrode lead 460 connected to the multi-port connector 450 via connectors 458 and 461. The lead 460 includes four electrodes 462, 463, 464, and 465 which are individually controllable by integrated circuit 452. Connectors 441 and 451 are employed to connect the lead 440 with multi-port connector 450. The length of lead 440 may vary greatly depending on the particular implanted configuration, where in some instances lead 440 may be 10 mm or longer, such as 25 mm or longer, including 50 mm or longer, as well as 100 mm or longer.

Figure 5:
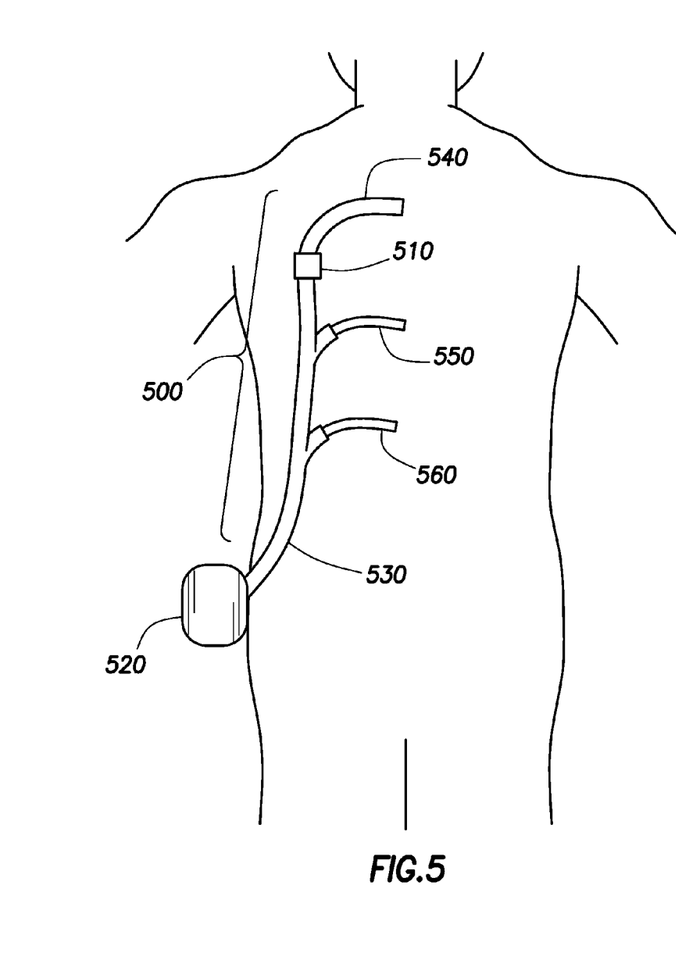
FIG. 5 provides a view of a multi-bus connector that may be present in a system according to the invention.

Another example of a multiplexed multi-electrode component that is made up of two or more subcomponents is shown in FIG. 5. The multiplexed multi-electrode component 500 includes a securing point 510, a control unit 520 and a multi-bus connector 530. The multi-bus connector 530 is electrically coupled to multiplexed lead elements 540, 550 or 560 along which the two or more individually addressable satellite electrode structures (not shown) are longitudinally positioned. The control unit 520 is operatively connected to the multiplexed multi-electrode component 500, such as through an IS-1 connector.

Figure 7:
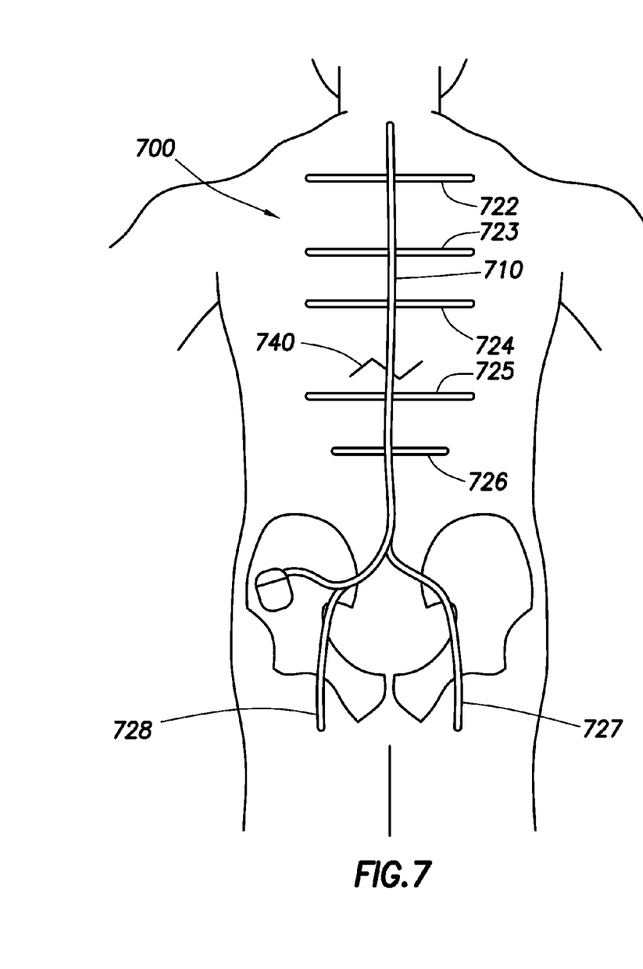
FIG. 7 provides a view of a branched percutaneous neurostimulation system according to the invention.

Devices of the invention may have a variety of configurations, including linear and branched. An example of a linear configuration is shown in FIG. 3A. An example of a branched configuration is shown in FIG. 7. In FIG. 7, device 700 includes a core multiplexed multi-electrode lead 710 with multiple branch leads 722, 723, 724, 725, 726, 727, and 728 in a configuration analogous to the naturally occurring nervous system having spinal cord and multiple spinal nerves which branch off the spinal cord. The core lead 710 and each branch have a multiplex configuration in which two wires run the length of the lead and multiple individually addressable satellite electrode structures are longitudinally positioned along the lead and coupled to the two wires in the core lead 710. Because of this multiplex configuration, each lead has a small outer diameter or low-profile. Where desired, each electrode may be employed to sense as well as stimulate. In this manner, breaks in the natural nervous system 740 can be bridged by sensing the nerve signal on one side of the break and then stimulating with the same signal on the other side of the break. The branched structure shown in FIG. 7 may be employed to replace a portion of a patient's nervous system or the entire nervous system, as desired.

As described above, multiplexed multi-electrode components of the devices may include one or more lead components. Lead components are elongated structures having lengths that are 2 times or longer than their widths, such as 5 times or longer than their widths, including 10, 15, 20, 25, 50, 100 times or longer than their widths. In certain instances, the leads have lengths of 10 mm or longer, such as 25 mm or longer, including 50 mm or longer, such as 100 mm or longer. A variety of different lead configurations may be employed, where the lead in various aspects is an elongated cylindrical structure having a proximal and distal end. The proximal end may include a connector element, e.g., an IS-1 connector, for connecting to a control unit, e.g., present in a "can" or analogous device. The lead may include one or more lumens, e.g., for use with a guidewire, for housing one or more conductive elements, e.g., wires, etc. The distal end may include a variety of different features as desired, e.g., a securing means, etc. Leads may be fabricated as flexible structures, where internal conductor elements may include wires, coils or cables made of a suitable material, such as alloy MP35N (a nickel-cobalt-chromium-molybdenum alloy), platinum, platinum-10 iridium, etc. The lead body may be any suitable material, such as a polymeric material, including polyurethane or silicone.

Lead components of the invention may have a variety of shapes, as desired. In some instances, the leads have a standard percutaneous shape, as found in conventional percutaneous neural stimulation leads. In some instances, the leads have a standard paddle shape, as found in conventional paddle neural stimulation leads.

Any of a variety of different protocols may be employed in manufacturing the devices of the invention. For example, molding, deposition and material removal, planar processing techniques, such as Micro-Electro-Mechanical Systems (MEMS) fabrication, may be employed. Deposition techniques that may be employed in certain aspects of fabrication of the devices or components thereof include, but are not limited to: electroplating, cathodic arc deposition, plasma spray, sputtering, e-beam evaporation, physical vapor deposition, chemical vapor deposition, plasma enhanced chemical vapor deposition, etc. Material removal techniques of interest include, but are not limited to: reactive ion etching, anisotropic chemical etching, isotropic chemical etching, planarization, e.g., via chemical mechanical polishing, laser ablation, electronic discharge machining (EDM), etc. Also of interest are lithographic protocols. Of interest in certain aspects is the use of planar processing protocols, in which structures are built up and/or removed from a surface or surfaces of an initially planar substrate using a variety of different material removal and deposition protocols applied to the substrate in a sequential manner.

In some instances, laser cut wires are employed as conductive elements for devices of the invention, such as for conductive elements of lead elements of devices of the invention. For example, conductive elements may be laser cut from a single sheet of metal. The pattern of the laser cut conductive elements may be chosen to match the positioning of the individually addressable satellite electrode structures of the lead. In this manner, the conductors and electrode structures may be aligned and then overlaid with the appropriate polymeric material to produce the desired lead structure. The laser cut conductive elements may have a variety of configurations from linear to curvilinear, sinusoidal or other fatigue resistance configuration. Instead of laser cutting, the conductor could also be fabricated using a deposition protocol, such as described above.

Devices of the invention may be implanted using any convenient protocol. Standard implantation procedures for percutaneous and paddle leads may be adapted for implantation of devices of the invention. The devices may be configured for ease of implantation. For example, devices may include a deployable element, such as lead components that inflate, e.g., with a gas or suitable liquid medium, to assume a desired configuration.

Also provided are systems that include one or more neural stimulation devices as described above operatively coupled to an implantable controller, which may be an implantable pulse generator. The implantable controller may be any suitable controller, including any of a number of implantable pulse generators currently employed for neurostimulation procedures, where the devices may be modified as desired to work with multiplexed multi-electrode neurostimulation devices of the invention. Also part of the systems may be any number of additional components, as desired, including extra-corporeal control units configured to transmit data and/or power to and/or receive data from the implantable components.

Also provided are methods of using the systems of the invention. The methods of the invention generally include: providing a system of the invention, e.g., as described above, that includes an implantable controller and neurostimulation device. The system may be implanted in a suitable subject using any convenient approach. Following implantation, the system may be employed to as desired to treat a condition of interest.

Figure 6A:
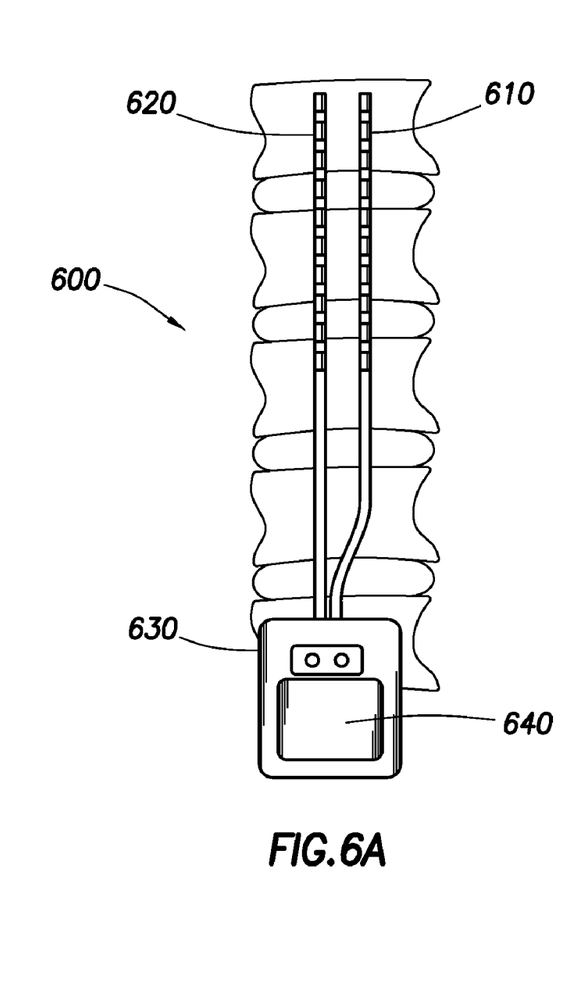
FIGS. 6A to 6C provide views of a percutaneous neurostimulation system according to another aspect of the invention.
Figure 6B:
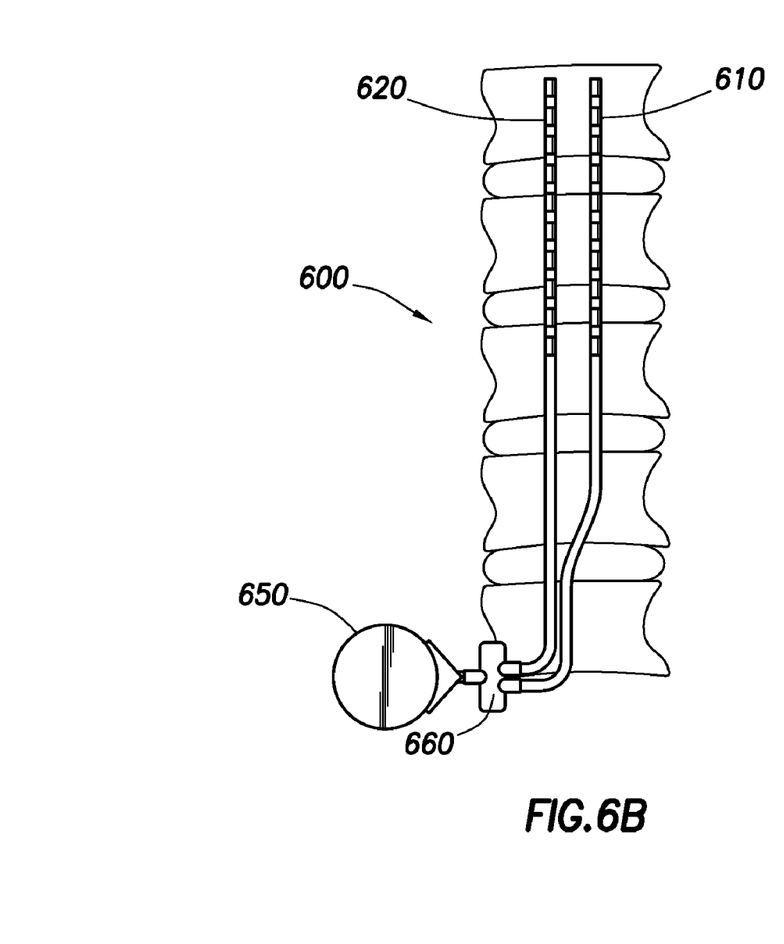
Figure 6C:
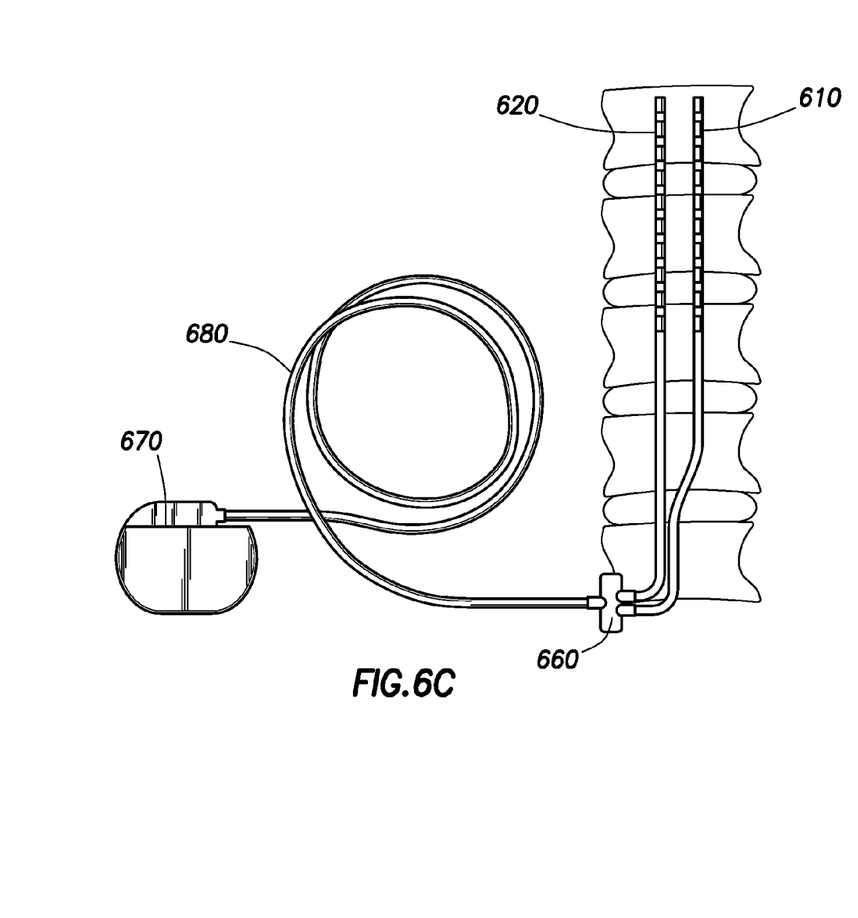

FIGS. 6A to 6B show examples of systems and methods for their use. In FIG. 6A system 600 includes two multiplexed multi-electrode leads 610 and 620 initially positioned such that they emerge from the body at port 630. Leads 610 and 620 are coupled to an external control unit 640 which provides power and also allows modification of programming. As shown in FIG. 6B, once the system 600 has been implanted and initially programmed, the external control unit 640 of FIG. 6A is replaced with internal control unit 650, which is connected to leads 610 and 620 by connector 660. FIG. 6C shows a variation of the system in FIG. 6B, where leads 610 and 620 are connected to remotely implanted control unit 670 via connector 660 and extender 680.

During use, a health care professional, such as a physician or other clinician, may select values for a number of programmable parameters in order to define the neurostimulation therapy to be delivered to a patient. For example, the health care professional may select a voltage or current amplitude and pulse width for a stimulation waveform to be delivered to the patient, as well as a rate at which the pulses are to be delivered to the patient and a duty cycle. The health care professional may also select as parameters particular electrodes within the electrode set carried by the leads to be used to deliver the pulses, and the polarities of the selected electrodes. A group of parameter values may be referred to as a program in the sense that they drive the neurostimulation therapy to be delivered to the patient.

A health care professional may select parameter values for a number of programs to be tested on a patient during a programming session, for example as provided in FIG. 6A, using a programming device. The programming device directs the implantable neurostimulator implanted in the patent to deliver neurostimulation according to each program, and the health care professional collects feedback from the patient, e.g., rating information, for each program tested on the patient. The health care professional then selects one or more programs for long-term use by the implantable neurostimulator based on the rating information.

Implantable neurostimulators device of the invention may be employed in a variety of different applications. Examples of applications include the use of the devices and systems to deliver neurostimulation therapy to patients to treat a variety of symptoms or conditions such as chronic pain, tremor, Parkinson's disease, epilepsy, incontinence, or gastroparesis. Typically, implantable neurostimulators deliver neurostimulation therapy in the form of electrical pulses via leads that include electrodes. To treat the above-identified symptoms or conditions, for example, the electrodes may be located proximate to the spinal cord, pelvic nerves, or stomach, or within the brain of a patient.

Figure 8:
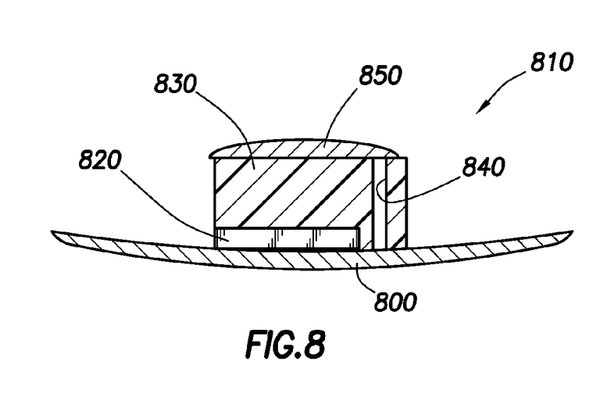
FIG. 8 provides a view of an individually addressable satellite electrode structure that includes a single electrode.

FIG. 8 provides a cross-section view of a laser cut conductive element 800 of an individually addressable satellite electrode structure 810. Integrated circuit component 820 is in electrical contact with laser cut conductive element 800. Conformal void free layer 830 is present on top of integrated circuit 820 and, upon overlay of the polymeric coating, hermetically seals the integrated circuit 820. Deposited single electrode 850 is present on top of layer 830 and connected to circuit 820 via connector 840. Electrode 850 may be deposited using any convenient protocol, such as cathodic arc deposition.

Figure 9:
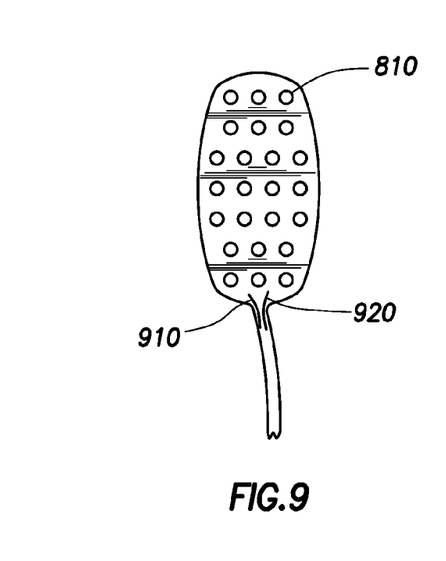
FIG. 9 provides a view of a paddle lead of the invention that includes the individually addressable satellite electrode structure shown in FIG. 8.

FIG. 9 shows a paddle lead 900 that includes multiple individually addressable satellite electrode structures 810. Underlying the shown electrode structures 810 may be a laser cut pattern of conductive elements as described above. As shown, all of the electrode structures 810 of the paddle 900 are coupled to two wires 910 and 920 such that the paddle 900 has a multiplexed configuration.

Also provided are kits that include the devices or components therefore, e.g., lead elements, connector elements, controllers, etc. In various aspects of the subject kits, the kits will further include instructions for using the subject devices or elements for obtaining the same (e.g., a website URL directing the user to a webpage which provides the instructions), where these instructions are typically printed on a substrate, which substrate may be one or more of: a package insert, the packaging, reagent containers and the like. In the subject kits, the one or more components are present in the same or different containers, as may be convenient or desirable.

It is to be understood that this invention is not limited to particular aspects described, as such may vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual aspects described and illustrated herein has discrete components and features which may be readily separated from or combined with the features of any of the other several aspects without departing from the scope or spirit of the present invention. Any recited method can be carried out in the order of events recited or in any other order which is logically possible.

What is claimed is:

1. An implantable device for target site stimulation, the device comprising:
   a multiplexed lead comprising at least one conductor;
   a plurality of multiplexed addressable units secured at predetermined locations along the conductor, wherein each addressable unit comprises:
      a multi-port connector defining a plurality of ports, wherein each port receives an electrode lead that is electrically coupled to and secured to the multi-port connector and each electrode lead includes a plurality of independently excitable electrodes; and
      a plurality of independently addressable integrated circuits corresponding to the number of defined ports in a the multi-port connector, wherein each circuit is electrically coupled to the corresponding electrode lead at the corresponding port and wherein each circuit controls the power flowing to each of the plurality of independently excitable electrodes of the respective electrode lead in the corresponding port; and
   a hermetically sealed control unit electrically coupled to the conductor, wherein the control unit provides control information and power to each of the plurality of multiplexed addressable units through the conductor;
   wherein the target site is a spinal nerve and wherein the device is shaped to at least partially surround the spinal nerve and wherein the multiplexed lead further comprises a second conductor secured and electrically coupled to at least a portion of the plurality of addressable units.

2. The implantable device of claim 1 wherein the multiplexed addressable units are arranged and multiplexed in a branched configuration.

3. An implantable device for target site stimulation, the device comprising:
   a multiplexed lead comprising at least one conductor;
   a plurality of multiplexed addressable units secured at predetermined locations along the conductor, wherein each addressable unit comprises:
      a multi-port connector defining a plurality of ports, wherein each port receives an electrode lead that is electrically coupled to and secured to the multi-port connector and each electrode lead includes a plurality of independently excitable electrodes; and
      a plurality of independently addressable integrated circuits corresponding to the number of defined ports in a the multi-port connector, wherein each circuit is electrically coupled to the corresponding electrode lead at the corresponding port and wherein each circuit controls the power flowing to each of the plurality of independently excitable electrodes of the respective electrode lead in the corresponding port; and
   a hermetically sealed control unit electrically coupled to the conductor, wherein the control unit provides control information and power to each of the plurality of multiplexed addressable units through the conductor;

wherein:

at least one electrode lead comprises four independently excitable electrodes that are uniformly and axially positioned about the respective electrode lead; and at least one other electrode lead comprises six independently excitable electrodes.

4. The implantable device of claim 3 wherein the six independently excitable electrodes are uniformly and axially positioned about the respective electrode lead.

5. The implantable device of claim 3 wherein the plurality of independently excitable electrodes of at least one electrode are positioned radially about the respective electrode lead.

6. The implantable device of claim 3 wherein the plurality of independently excitable electrodes of at least one electrode lead are positioned on one side of the respective electrode lead.

7. The implantable device of claim 3 wherein the plurality of independently excitable electrodes of at least one electrode lead are staggered along the respective electrode lead.

8. The implantable device of claim 7 wherein the system further comprises a power storage unit coupled to the conductor of the lead for supplying power to the electrode structures through the integrated circuit controller.

9. The implantable device of claim 7 wherein the plurality of independently addressable integrated circuits are hermetically sealed.

* * * * *